United States Patent [19]

Harrington et al.

[11] Patent Number: 5,107,855
[45] Date of Patent: Apr. 28, 1992

[54] APENA MONITOR FOR DETECTION OF APERIODIC SINUSOIDAL MOVEMENT

[75] Inventors: Reginald Harrington; Ralph Crossley, both of Winnipeg, Canada

[73] Assignee: RKR Corporation, Winnipeg, Canada

[21] Appl. No.: 490,713

[22] Filed: Mar. 8, 1990

[51] Int. Cl.⁵ ............................................... A61B 5/02
[52] U.S. Cl. ..................................... 128/721; 128/782
[58] Field of Search ................ 128/721, 722, 723, 716, 128/774, 782

[56] References Cited

U.S. PATENT DOCUMENTS

| | | | |
|---|---|---|---|
| 4,146,885 | 3/1979 | Lawson, Jr. | 340/573 |
| 4,296,757 | 10/1981 | Taylor | 128/721 |
| 4,308,872 | 1/1982 | Watson et al. | 128/721 |
| 4,433,693 | 2/1984 | Hochstein | 128/721 |
| 4,619,270 | 10/1986 | Margolis et al. | 128/721 |
| 4,646,307 | 9/1987 | Montigieux | 128/721 |
| 4,738,264 | 4/1988 | Orlando | 128/721 |
| 4,846,462 | 7/1989 | Regnier et al. | 128/781 |
| 4,884,578 | 12/1989 | Morgenstern | 128/721 |
| 4,909,260 | 3/1990 | Salem et al. | 128/721 |
| 4,967,751 | 11/1990 | Stezer | 128/721 |

FOREIGN PATENT DOCUMENTS 1007302 3/1977 Canada.

Primary Examiner—Kyle L. Howell
Assistant Examiner—S. Akers
Attorney, Agent, or Firm—Adrian D. Battison; Stanley G. Ade; Murray E. Thrift

[57] ABSTRACT

An apena monitor detects breathing movement by a strap attached around the thorax region of the patient together with a Hall effect detector which is arranged to detect expansion movements of the body of the patient. The detector includes a first part mounted on one part of the strap and a transducer element attached to a second part of the strap so as to be pulled away from the first part against the bias of a spring and released toward the first part in dependence upon the movement. The position of the transducer element relative to the first part is transmitted wirelessly to a receiver using an antenna mounted on the bed frame construction. The signals are decoded to produce a series of values each dependent upon an instantaneous position of the transducer element. The values are monitored to detect increasing and decreasing values indicative of an aperiodic sinusoidal pattern associated with breathing.

9 Claims, 7 Drawing Sheets

APENA MONITOR FOR DETECTION OF APERIODIC SINUSOIDAL MOVEMENT

BACKGROUND OF THE INVENTION

This invention relates to a device for detecting movement of muscles of a human body which is particularly but not exclusively designed for monitoring breathing patterns during sleep for use for example as a sleep apnea alarm.

Various previous sleep apnea alarm devices have been proposed for monitoring the breathing particularly of infants during sleep but also the breathing of adults who may have breathing difficulties.

There are a number of areas of difficulty in such devices and these difficulties have to date substantially prevented any effective device from being available in the marketplace.

Firstly there is the difficulty of initially detecting the movement of the muscles. Many arrangements have used devices which detect pressure changes caused by movement of the patient on a mattress but these devices have proven to be unreliable. Alternative techniques use a band or similar equipment attached around the patient particularly in the thoracic area. The extension and contraction of the band is then detected in some cases by strain guages and in other cases by movement of one element which varies a capacitive coupling. Again these devices have proven to be unreliable.

A second area of difficulty relates to the communication of the information from the detecting device to a receiving device mounted separately from the patient. In most cases a wire coupling is used but this is of course highly unsatisfactory and it can restrict movement of the patient and can be dangerous should the patient become entangled in the wire coupling.

A third area of difficulty relates to the analysis of the information from the detection device mounted on the patient. In most cases the analysis is very simplistic and can fail to distinguish between the required breathing patterns and any other type of movement.

Basically therefore it is absolutely essential in a device of this type to provide a device which is reliable in that it acts to trigger an alarm whenever breathing difficulties are encountered but at the same time the device must be able to properly distinguish from other conditions caused for example by movement of the patient away from a preferred detecting location which would cause the alarm to be actuated when no emergency condition is present. Such an alarm device which produces a number of false alarms will of course rapidly lose any credibility and will no longer be used.

Examples of devices of this type are shown in U.S. Pat. Nos. 4,146,885 (Lawson), 4,296,757 (Taylor), 4,433,693 (Hochstein) and 4,619,270 (Margolis). A further example is shown in Canadian patent 1,007,302 (Hardway).

U.S. Pat. No. 4,146,885 discloses a technique using pressure detection within a closed chamber underneath a membrane on which the patient lies. This technique has been found to be highly inaccurate and unsatisfactory for reliable detection.

U S. Pat. No. 4,296,757 discloses a simple mechanical switch attached to the patient with the improvement relating to a cushion device which protects the mechanical switch from being deactivated when the patient rolls over onto the position where the switch is located.

U.S. Pat. No. 4,433,693 discloses a device in which movement causes a variation in a capacitance to vary the tuning frequency of a tuned circuit. This variation is detected by transmission of a radio frequency electro magnetic field around the device attached to the patient and by detecting the variations in resonance. This device is apparently not commercially available and is unlikely to have the required accuracy of detection.

U.S. Pat. No. 4,619,270 discloses a stimulating device which acts to move the bed construction on which the patient lies to cause stimulation in an alarm condition.

Canadian Patent 1,007,302 discloses a pad on which the patient lies with movement of the patient causing variation in capacitance of a detection system within the pad. Again this device is unlikely to provide the necessary level of detection accuracy.

SUMMARY OF THE INVENTION

It is one object of the present invention, therefore, to provide an improved monitoring device of this general type.

It is a further object of the present invention to provide a device which is of small size so that it can be readily attached to the patient without interfering with the normal movements of the patient.

It is a further object of the present invention to provide a device which has a high level of sensitivity so that it can detect readily alarm conditions and can avoid false alarms.

It is a further object of the invention to provide a device which has wireless communication between the detection device attached to the patient and a receiver mounted separately from the patient.

It is a further object of the invention to provide a technique for analysis of the signals emitted by the detection device which enables accurate detection in an alarm condition without false alarms.

It is a yet further object of the invention to provide an improved stimulation or nudging device which can be actuated if required so as to cause a nudging action periodically to help prevent breathing difficulties from arising, and in addition it can be be actuated automatically in an alarm condition to cause stimulation of the patient lying on the bed construction.

According to a first aspect of the invention, therefore, there is provided an apparatus for detecting movement of muscles of a human body comprising a first element, a second element, means for mounting the elements on the body such that movement of the muscles cause relative movement of the elements in a direction to increase and decrease the spacing therebetween, means for detecting said relative movement and for translating said movement into signals indicative of said movement, and a receiving station for receiving said signals having means for decoding said signals, said detecting means comprising a magnet mounted on said first element and a Hall effect means mounted on the second element such that the position of the magnet relative to the Hall effect means causes a variation in the output of the Hall effect means and means responsive to the output of the Hall effect means for generating signals.

According to a second aspect of the invention, therefore, there is provided an apparatus for detecting movement of muscles of a human body comprising a first element, a second element, means for mounting the elements on the body such that movement of the muscles cause relative movement of the elements in a direction to increase and decrease the spacing therebetween, means for detecting said relative movement and for translating said movement into signals indicative of said movement, and a receiving station for receiving such signals having means for decoding such signals, the second element including means for translating said signals into a radio frequency signal and antenna means for transmitting said radio frequency signal.

According to a third aspect of the invention, therefore, there is provided an apparatus for detecting breathing patterns of a human body during sleep comprising a first element, a second element, means for mounting the elements on the body such that movement of the muscles cause relative movement of the elements in a direction to increase and decrease the spacing therebetween, means for detecting said relative movement and for translating said movement into signals indicative of said movement, and a receiving station for receiving such signals having means for decoding such signals, said receiving means including an antenna mounted on a bed construction on which the human body is placed, said receiving means including means for detecting an alarm condition in which the absence of movement over a period of time is detected and means for actuating movement of the bed construction in response to said alarm condition and wherein the bed construction includes a mattress having an upper surface including a substantially flat central portion and inclined portions around the periphery extending upwardly from the central portion and thus forming a substantially concave upper surface and wherein the moving means comprises a plate member on an underside of the mattress and means for moving the plate member in a vertical reciprocating action to cause vibration of the mattress.

With the foregoing in view, and other advantages as will become apparent to those skilled in the art to which this invention relates as this specification proceeds, the invention is herein described by reference to the accompanying drawings forming a part hereof, which includes a description of drawings forming a part hereof, which includes a description of the best mode known to the applicant and of the preferred typical embodiment of the principles of the present invention, in which:

DESCRIPTION OF THE DRAWINGS

In the drawings like characters of reference indicate corresponding parts in the different figures.

DETAILED DESCRIPTION

Figure 1:
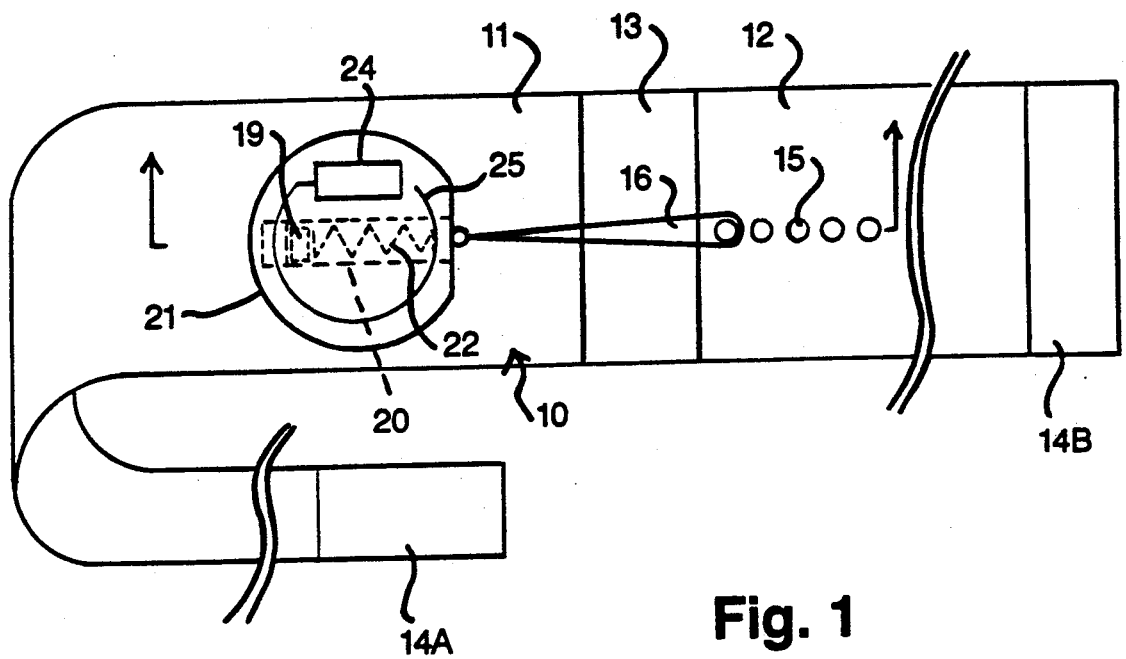
FIG. 1 is a plan view of the detection device for mounting upon the body of the patient.

Turning firstly to FIG. 1 there is shown a detector assembly for mounting upon the body of a patient and particularly the thoracic area of the patient. The present device is particularly but not exclusively designed for use with infants to detect the muscular movement generated by the breathing action. The detection device comprises a belt construction 10 which is formed in two portions indicated respectively at 11 and 12 connected by an elastic section 13 which allows relative movement or expansion to occur at the elastic section allowing the parts 11 and 12 to move inwardly and outwardly in dependance upon movement of the muscles around which the belt is wrapped. The belt has suitable fastening mechanisms at the ends so that it can be connected together as a complete loop surrounding the body of the patient. In one example the fastening is provided by a hook and loop pile fabric fastening arrangement indicated at 14A, 14B.

Figure 2:
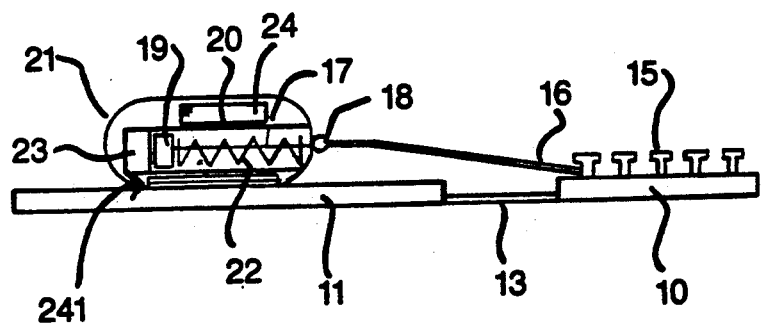
FIG. 2 is a cross sectional view along the lines 2—2 of FIG. 1.

The strap portion 12 includes a plurality of upstanding buttons or hooks 15 arranged in spaced relationship on a line at right angles to the width of the strap. A flexible loop member 16 includes an opening which allows it to be fastened over a chosen one of the buttons 15. The other end of the loop member is connected to an elongate non-ferrous pin 17 with a loop 18 on the outer most end for connection to the loop member 16. The pin carries a magnet 19 slidable along a guide track 20 arranged longitudinally of the strap and mounted in a housing 21 attached to the strap portion 11. A spring 22 biases the magnet 19 in a direction toward the left hand end of the track 20 as shown in FIG. 2 so that movement of the magnet takes places against the force provided by the spring 22. It will be appreciated therefore that, as the two parts of the strap are moved apart by expansion of the muscles of the patient, the magnet 19 moves up and down longitudinally of the track 20 to a position dependant upon the degree of expansion.

The position of the magnet 19 is measured by a Hall effect device 23 mounted within the housing 21 in a fixed position at the end of the track 20. The operation of a Hall effect device is a conventional technique and is well known. It does however provide an effective and accurate detection of the position of the magnet 19 providing an output which is linearly dependant upon the position of the magnet.

The output from the Hall effect device 23 is communicated to a control unit 24 mounted also within the housing 21.

Figure 3:
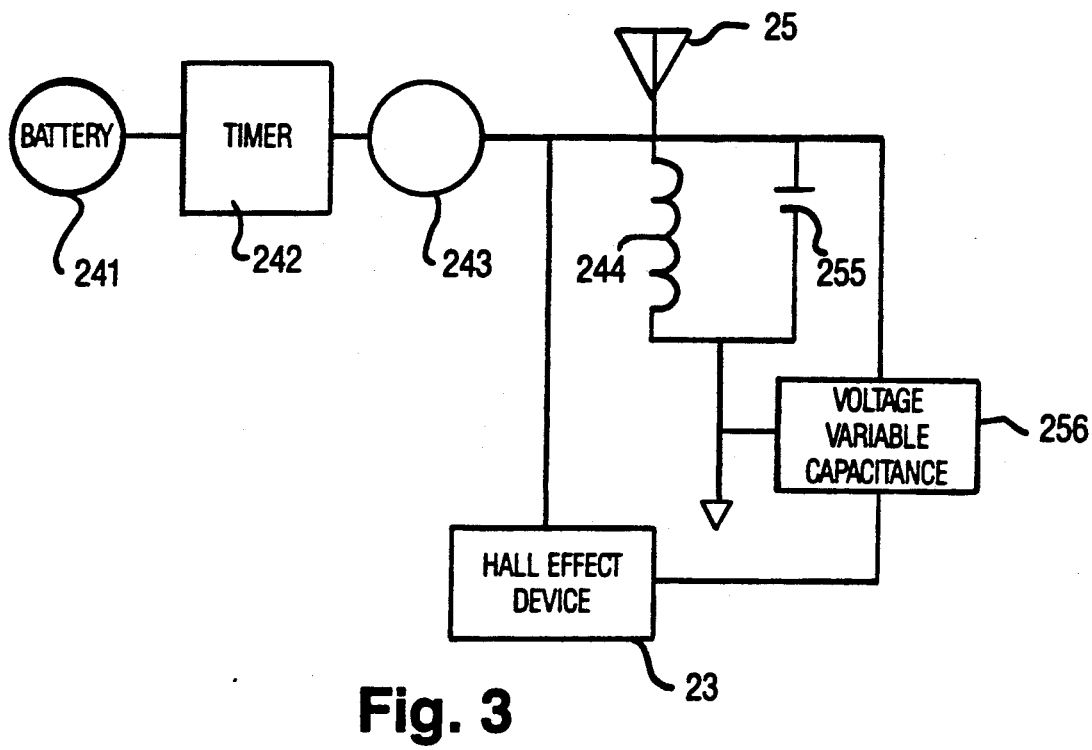
FIG. 3 is a schematic block diagram showing the circuit of the detector device.

The details of the control unit are shown in FIG. 3, and comprises a 6 volt battery 241, a timer 242, a power transistor 243, and an antenna 25 and a frequency variation circuit including an inductor 244, a capacitor 255, a voltage variable capacitor 256 and the Hall effect device 23.

The control unit 24 thus includes the timing device 242 which operates the unit intermittently to detect at periodic intervals the instantaneous position of the magnet 19. This periodic detection provides an output from the Hall effect device which is used to vary the frequency of the electromagnetic wave transmitted by the antenna 25. As shown in FIG. 1, the antenna is mounted in the top part of the housing 21 and thus the whole unit is self contained and relatively small. The amount of power used is maintained to a minimum so that the device can be powered by the battery shown in FIG. 3. The output power from the transmittor to the antenna 25 can be maintained at a minimum at a very low level of for example 5 milliwatts.

Figure 4:
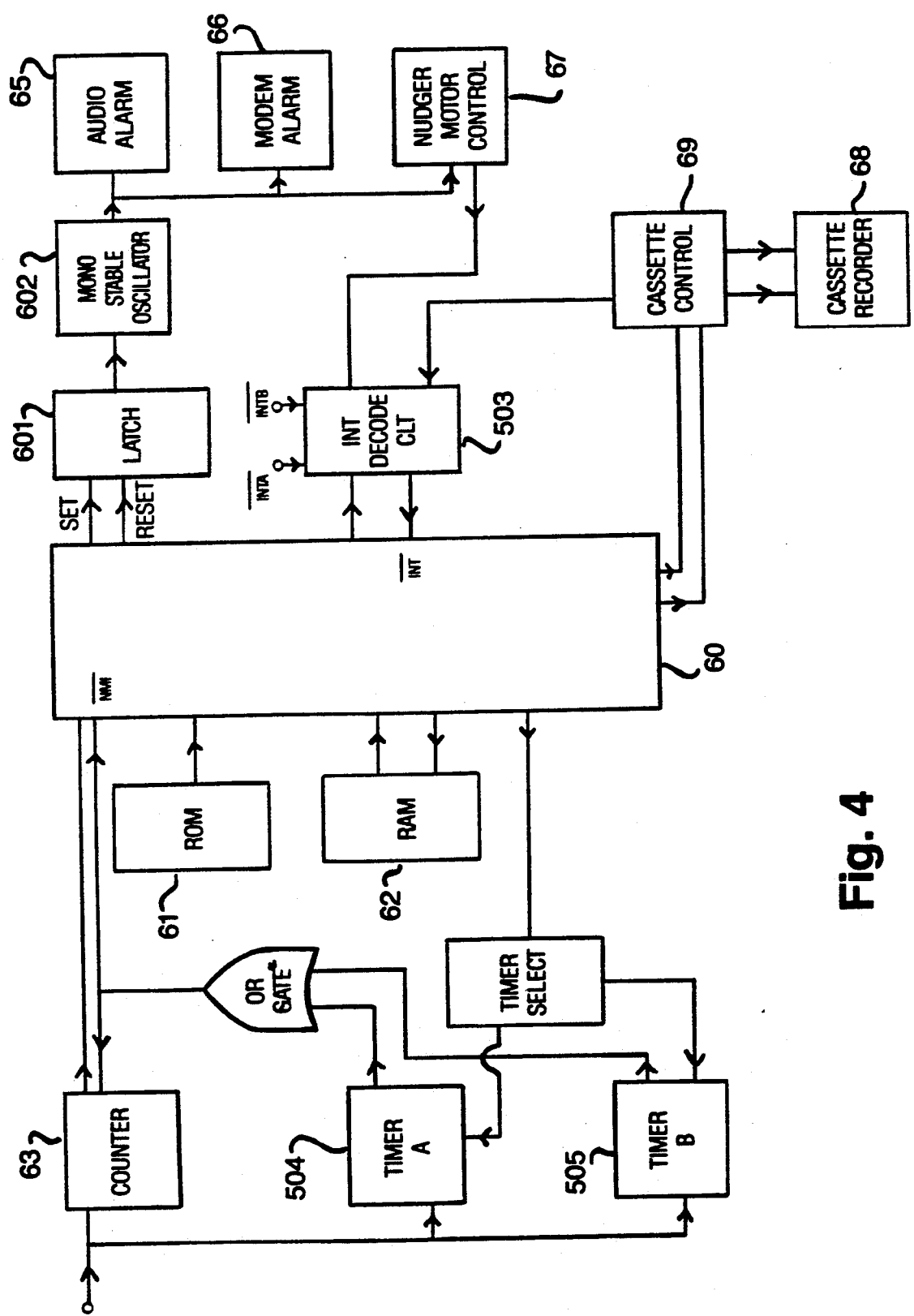
FIG. 4 is a schematic block diagram of the circuit of the control unit.
Figure 5:
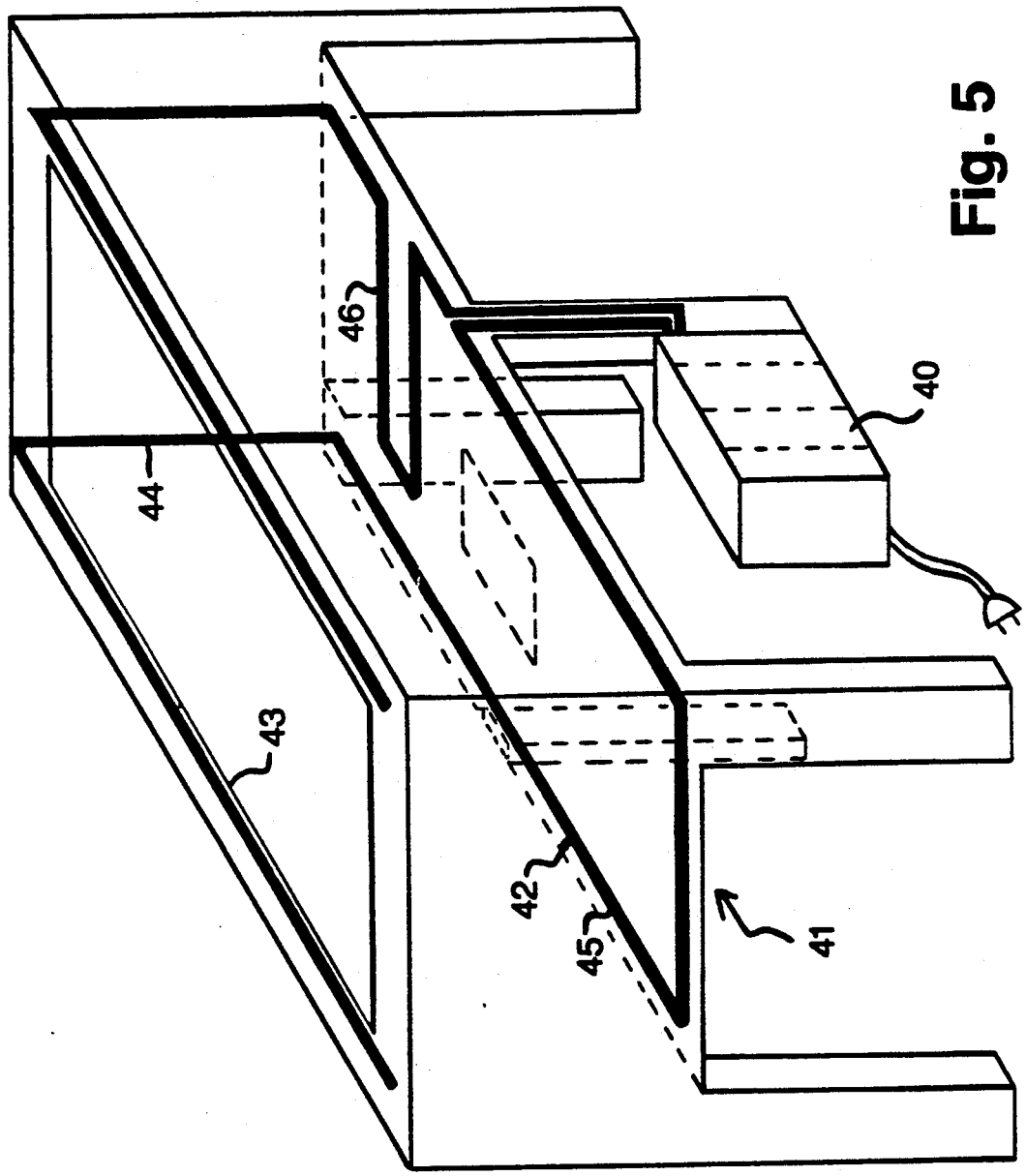
FIG. 5 is an isometric view of the frame of a crib for receiving the patient and showing particularly the antenna construction.

Turning now to FIGS. 4 and 5, the receiving unit is shown. In FIG. 5, the receiving unit is indicated at 40 mounted adjacent a bed construction 41 on which the patient is laid. In this case the bed constructed is in a form of a crib for an infant. A full wave antenna 42 is mounted within the frame of the crib in a position so that it surrounds the patient and particularly the transmitting device of the patient thus allowing the power to be maintained at a minimum. Specifically the antenna includes two legs one of which includes a portion running along the top of the frame indicated at 43, a vertical section 44, a horizontal section 45 along the lower part of the frame along one side and along one end. The second leg is similarly arranged but includes an additional loop 46 so that its length is equal to the length of the first leg of the antenna.

Figure 6:
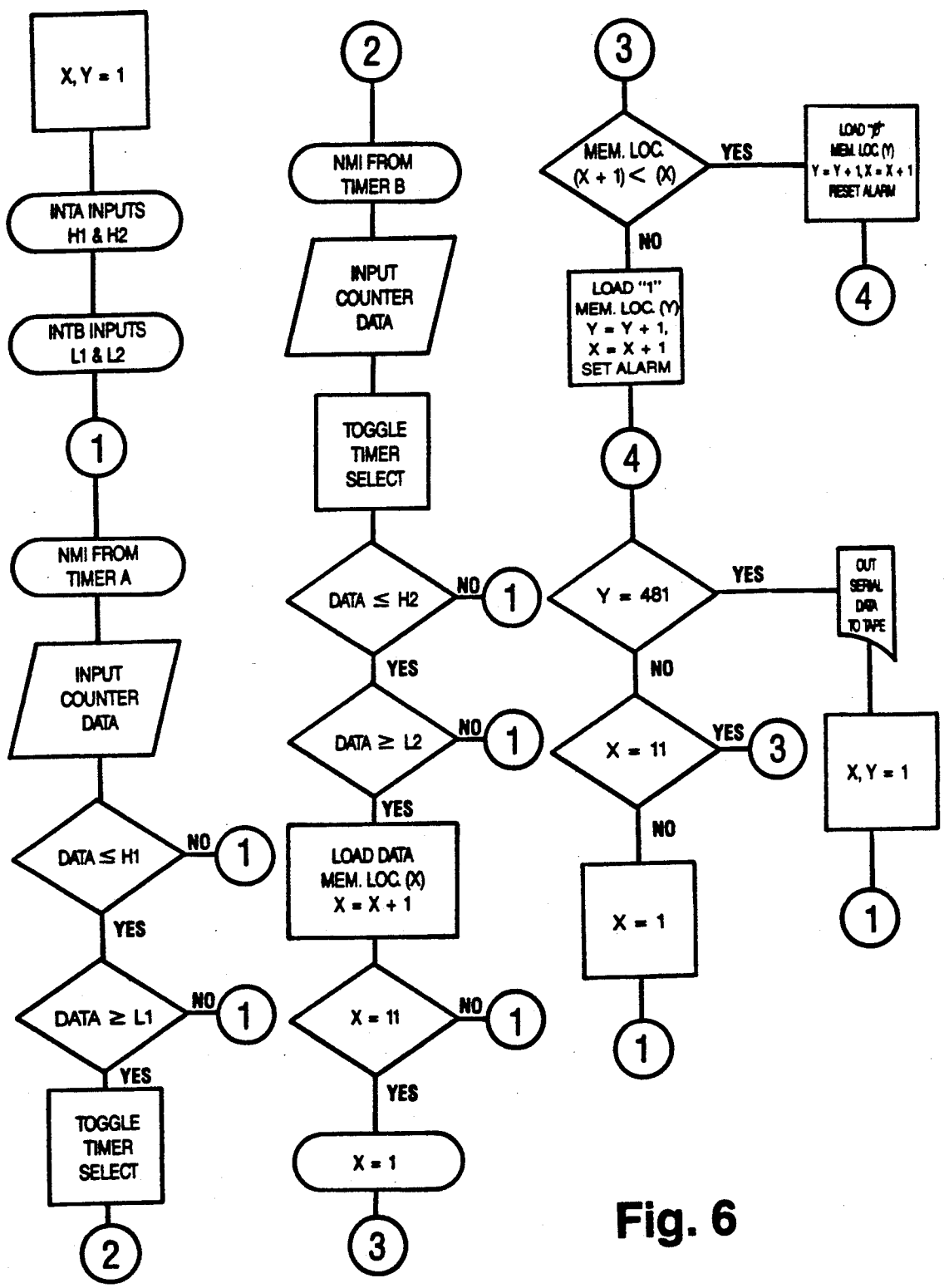
FIG. 6 is a flow chart showing the analysis procedure.
Figure 10:
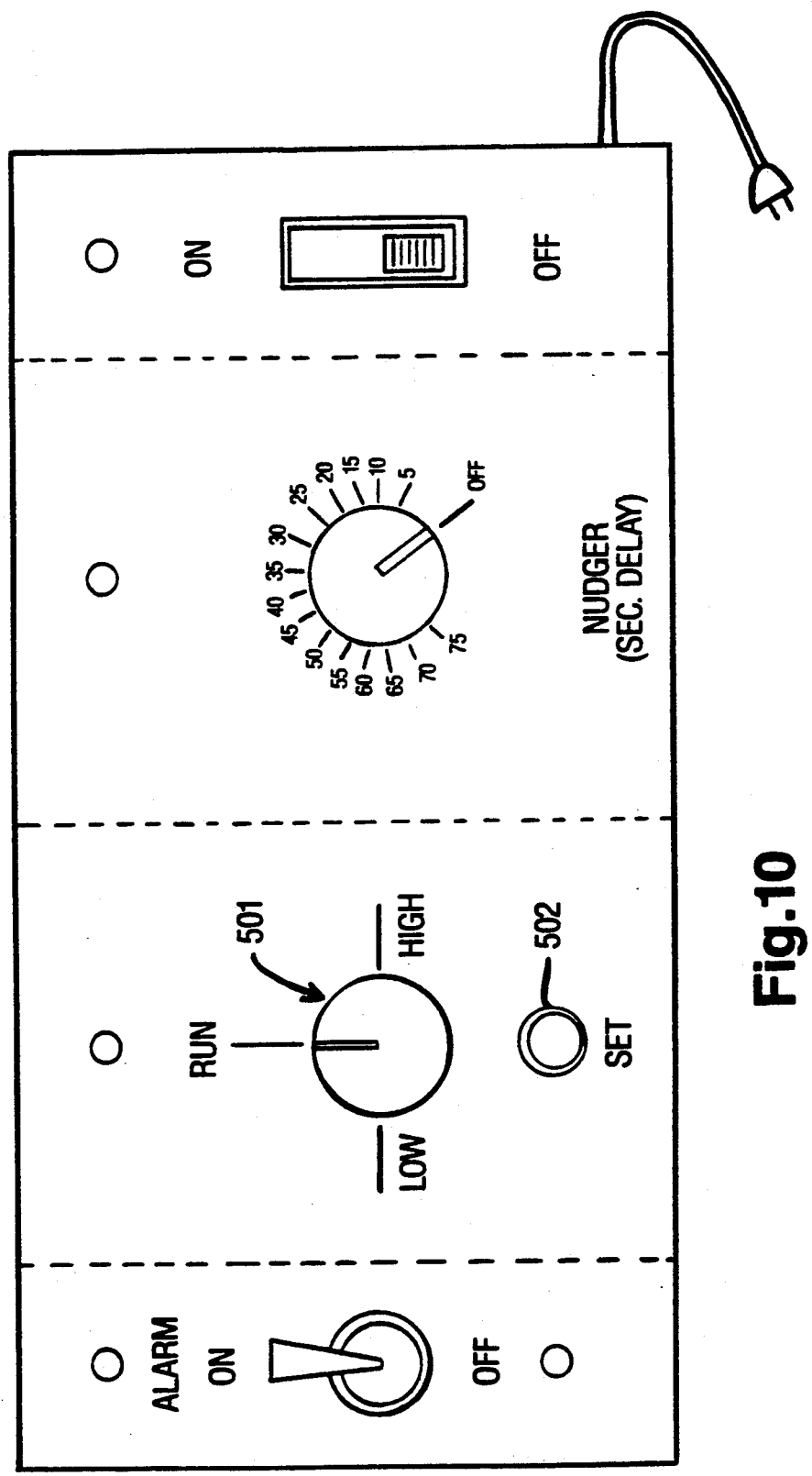
FIG. 10 is a front elevational view of the control unit.

Turning now to FIG. 4, the block diagram of the operation of the receiver device is shown. In addition in FIG. 6 is shown the flow chart of the analysis procedure by which the signals transmitted from the detection device on the patient are received and analyzed allowing the alarm condition to be detected. FIG. 10 shows the main manual controls and switches of the control unit.

Specifically the receiving device includes a microprocessor 60 which controls the analysis procedure using data from the ROM 61 and the necessary RAM 62. The microprocessor controls the operation of a counter 63 which detects the frequency of the signal received from the antenna 42.

Output from the microprocessor comprises an alarm flip-flop 601 which retriggers a monostable oscillator 602. Failure to retrigger 602 generate an alarm enable signal which provides a signal to a speaker 65 and to a modem 66, the latter allowing communication to a remote location. At the same time the alarm enable signal actuates a nudger motor control 67 as shown in more detail in FIGS. 7 and 8.

In addition to the alarm enable output, a second output to the cassette control unit, 69, enables information on the analyzed movement patterns to be output to a tape cassette 68 and a third output controls the cassette tape deck power allowing storage of data relating to the movement patterns. This information can be output in a data stream after colation of the data by the microprocessor so that relatively long periods of information can be stored on high speed basis.

The control unit 24 is initialized with power on and the alarm disabled. The initialization dial 501 firstly is switched manually to the LOW setting. The magnet of the sensor is allowed to move to an initial relaxed position, the SET momentary button 502 is pressed. A pulse $\overline{INTA}$ is manually output to and the interrupt decode circuit 503 which generates an $\overline{INT}$ pulse to the microprocessor unit MPU 60. The MPU responds by enabling timer A 504 (a 2 mSec. monostable) and storing the resultant count rate labelled. L1, in RAM 62. Then the MPU enables timer B, 505, (a 10 mSec. monostable) and stores the resulting count rate as L2 in RAM 62.

Next the user switches the initialization dial 501 to the HIGH setting and manually pulls the magnet of the sensor to full extension then presses the SET button. A pulse ($\overline{INTB}$) is output to the interrupt decode circuit 503 which generates a $\overline{INT}$ pulse to the MPU. The MPU services the interrupt by enabling timer A,504, and storing the pulses counted in a 2 mSec. period as H1 in RAM 62. Then the MPU enables timed B, stores a 10 mSec period count rate as H2 in RAM. Finally the initialization dial 501 is switched to RUN, the sensor is attached to the patient and the alarm is enabled. This procedure thus calibrates the sensor between the initial rest or minimum displacement position and a position of maximum extension or displacement.

The pulse train demodulated by the receiver is input to the counter 63, timer A and timer B inputs. Initially timer A is enabled for 2 mSec. and enables the counter for the same period. The negative edge of the timer A output triggers the $\overline{NMI}$ (non-maskable interrupt) input to the MPU. The MPU inputs the count rate and compares the data to H1 and L1. If the data is larger than H1 or smaller than L1, control is returned to 1 (FIG. 6). If the data fits the window then timer B and the counter are enabled for 10 mSec. by the next data pulse. The resulting count is input to the MPU by $\overline{NMI}$ as before. The data is verified as greater than L2 and less than H2 then stored in RAM. If the data does not fit the window then the timer select is toggled to enable timer A and control is returned to 1.

After 5 seconds of data (10 readings), the data is analyzed. The MPU compares each data byte with the previous data byte. If the value of the data increases, "11111111" is output to memory location (Y) and (Y) is incremented. If the data value decreases then "00000000" is output to (Y) and (Y) is incremented. If the value is increased a pulse is output to the SET input of the alarm latch. If the value decreased a pulse is output to the RESET input of the alarm latch. The output of the alarm latch retriggers the adjustable monostable oscillator. If the monostable is not retriggered in a selected predetermined period, that is the MPU does not detect both an increased and a decreased value within said time period indicative of the presence of an observable aperiodic sinusoidal pattern, then the alarm signal is output. When 4 minutes of data (Y=481) is stored in RAM, the MPU triggers a 4 second timer to enable the cassette power supply, and outputs the data in a serial pulse train. Finally the registers are reset and control returns to (1).

Figure 8:
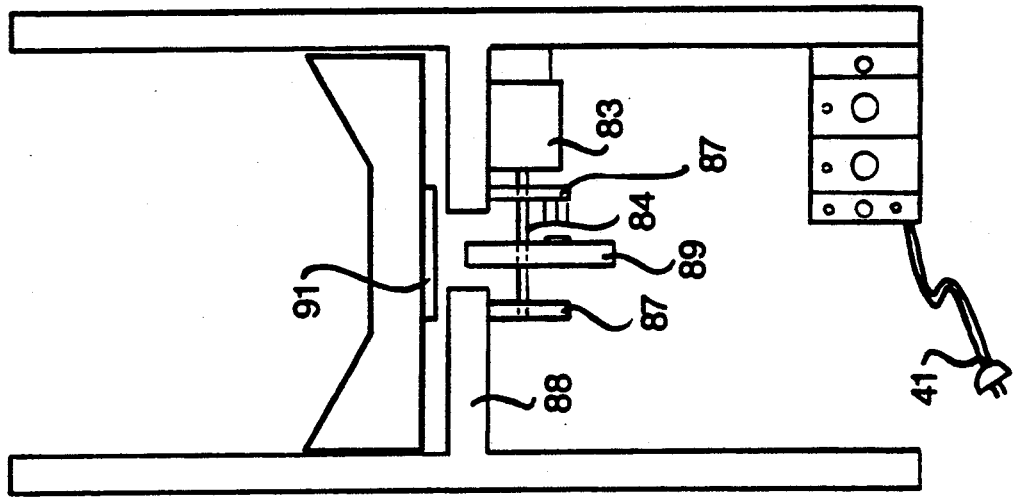
FIG. 8 is a cross sectional view along the lines 8—8 of FIG. 7.
Figure 7:
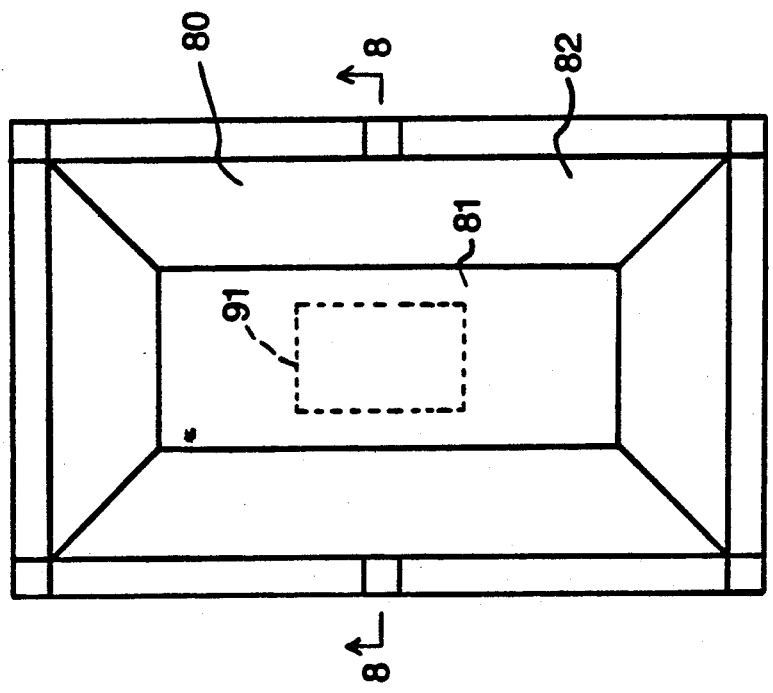
FIG. 7 is a top plan view of the crib of FIG. 5 showing the mattress and oscillator plate.

Turning now to FIGS. 7 and 8, further detail of the crib and of the nudger control are shown, the latter providing the reciprocating action of the mattress which allows stimulation of the patient in regular operation if actuated and in the event that an alarm condition is detected. The crib comprises the frame as shown in FIG. 5 within which is mounted a mattress 80. The mattress has a substantially concave upper surface including a flat central section 81 together with a plurality of inclined outer sections 82. This acts to ensure that the patient remains on the central section despite the relatively vigorous reciprocating movement.

The control unit is indicated at 40 and receives power from a conventional electrical plug 41. An electric motor 83 is mounted on an underside of the mattress support and is controlled as previously explained by the output from the control unit 40 so that during regular operation or on an alarm condition the motor 83 is actuated. The motor 83 includes an output shaft 84 carried on fixed supports 87 mounted on the underside of the mattress support 88 of the crib frame. An eccentric 89 passes through an opening 90 in the bed support 88 for engagement with a plate 91 mounted on the underside of the mattress.

Feedback is via an infrared beam transmitted by a sender and reflected by reflective tape on the eccentric back to the receiver. The feed back prevents overrun of the nudger.

Figure 9:
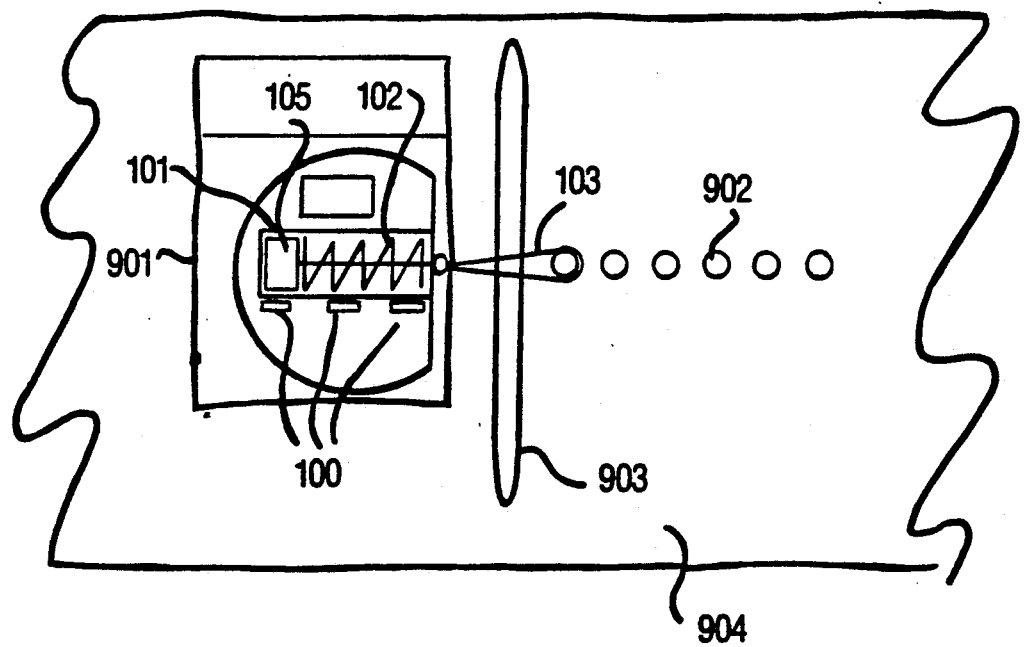
FIG. 9 is a schematic cross-sectional view of an alternative detector device arranged for mounting upon the clothing of the patient and including an alternative detector configuration.

Turning now to FIG. 9 an alternative arrangement of the device is shown for attachment to the patient. In this case the device does not include a band which wraps around the patient but merely includes a pocket 901 sewn on to the infant top so that the detector can be placed in the pocket to be attached to the clothing of the patient and a second element in the form of buttons 902 which attach to a second part of the clothing separated from the pocket by a slit 903 in the clothing 904.

In FIG. 9 it is also shown a different arrangement of the detection device in which there are provided three separate Hall effect devices 100 positioned at spaced positions along the length of the guide track 101. The loop 103 is attached via a flexible strap element to for example a button of the clothing of the patient. The spring 102 biases the magnet 105 to a position at the remote end of the guide track 101. As the magnet is moved along the guide track, it associates with one of the Hall effect devices 100. The Hall effect devices are arranged in a circuit which generates a different frequency for each of the Hall effect devices when actuated so that the signals transmitted by the device will have three different frequencies depending upon which Hall effect device is triggered.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

We claim:

1. Apnea monitor apparatus for detecting breathing movement of a human patient comprising attachment means including encircling means substantially fully encircling the girth of the patient adjacent the thorax area of the patient at a position thereon at which the girth increases and decreases in response to breathing movement, said encircling means defining an open area between two spaced portions thereof and being arranged such that the spacing between the two portions increases and decreases in response to said increase and decrease in girth, a detector means including a first element mounted on one of said portions, a second element mounted on the other of said portions, a connector extending across the open area from said first element to said second element such that the connector is pulled by said second element to move relative to said first element in a first direction longitudinal of said encircling means toward said second element across said open area by an increasing girth and released to move opposite to said first direction by a decrease in girth, a detector means attached to said connector so as to be movable from an initial rest position to a displaced position in said first direction spaced from the rest position, spring means connected between said detector means and said first element biassing said detector means against said relative movement in said first direction, sensor means mounted on said first element and arranged to generate a plurality of sequential output signals each proportional to an instantaneous detection of the displaced position of the detector means, means for transmitting the output signals, means for receiving the transmitted output signals, analysis means for analyzing the output signal to determine the absence of breathing movements and alarm means for providing an alarm signal in response to the absence of breathing movements.

2. The invention according to claim 1 arranged for detection of breathing patterns of the human body during sleep, said receiving means including an antenna mounted on a bed construction on which the human body is placed.

3. The invention according to claim 2 wherein the antenna comprises a full wave antennae attached to parts of the bed construction so as to surround the human body to provide detection of the transmissions from the second element while allowing minimum power usage for the transmission.

4. The invention according to claim 2 wherein the bed construction includes a mattress having an upper surface including a substantially flat central portion and inclined portions around the periphery extending upwardly from the central portion and thus forming a substantially concave upper surface and wherein there is provided moving means for actuating movement of the bed construction in response to said alarm condition comprising a plate member on an underside of the mattress and means for moving the plate member in a vertical reciprocating action to cause vibration of the mattress.

5. The invention according to claim 1 wherein the detector member comprises a magnet and wherein the sensor means comprises a single hall effect device mounted adjacent one end of a linear path of movement of the magnet of the first element such that movement of the magnet varies substantially linearly the output of the hall effect device.

6. The invention according to claim 1 wherein the analysis means comprises means for comparing each separate signal received of said plurality of sequential signals with a previous one of said signals so as to provide an output indicative of one of movement toward the first element, movement away from the first element, means for detecting a plurality of said outputs and means for generating an alarm condition in the absence of an observable aperiodic sinusoidal pattern in the outputs.

7. The invention according to claim 1 wherein the receiving means includes means for actuating a recording medium and means for applying to the recording medium data indicative of the movement of the muscles over a period of time.

8. Apnea monitor apparatus for detecting breathing movement of a human patient comprising attachment means including encircling means substantially fully encircling the girth of the patient adjacent the thorax area of the patient at a position thereon at which the girth increases and decreases in response to breathing movement, said encircling means defining an open area between two spaced portions thereof and being arranged such that the spacing between the two portions increases and decreases in response to said increase and decrease in girth, a detector means including a first element mounted on one of said portions, a second element mounted on the other of said portions, a connector extending across the open area from said first element to said second element such that the connector is pulled by said second element to move relative to said first element in a first direction longitudinal of said encircling means toward said second element across said open area by an increasing girth and released to move opposite to said first direction by a decrease in girth, a detector means attached to said connector so as to be movable from an initial rest position to a displaced position in said first direction spaced from the rest position, spring means connected between said detector means and said first element biassing said detector means against said relative movement in said first direction, sensor means mounted on said first element and arranged to generate a plurality of sequential output signals each proportional to an instantaneous detection of the displaced position of the detector means, means for transmitting the output signals, means for receiving the transmitted output signals, analysis means for analyzing the output signal to determine the absence of breathing movements and alarm means for providing an alarm signal in response to the absence of breathing movements, said sensor means being arranged to generate said output signals such that each output signal has associated therewith a numerical value the value of which is proportional to the distance of displacement of the respective displaced position from the rest position, wherein said analysis means comprises comparator means for comparing the value of each output signal received with the value of a next previous one of the output signals so as to provide either a first output indicative of an increased value or a second output indicative of a reduced value and means responsive to a series of said first and second outputs occurring in a predetermined time period to detect both an increased and a decreased value within said time period indicative of the presence of an observable aperiodic sinusoidal pattern in the series of first and second outputs.

9. Apnea monitor apparatus for detecting breathing movement of a human patient comprising a first element, a second element, means for mounting the elements on the body such that movement of the muscles cause relative movement of the elements in a direction to increase and decrease the spacing therebetween, sensor means for detecting said relative movement and for translating said movement into output signals indicative of said movement, and a receiving station including analysis means for receiving said signals having means for decoding said signal, said sensor means being arranged to generate said output signals such that each output signal has associated therewith a numerical value the value of which is proportional to the distance of displacement of a respective displaced position of one of said elements relative to the other from the rest position, wherein said analysis means comprises comparator means for comparing the value of each output signal received with the value of a next previous one of the output signals to provide either a first output indicative of an increased value or a second output indicative of a reduced value and means responsive to a series of said first and second outputs occurring in a predetermined time period to detect both an increased and a decreased value within said time period indicative of the presence of an observable aperiodic sinusoidal pattern in the series of first and second outputs and means for generating an alarm condition in the absence of said aperiodic sinusoidal pattern observed in said period.

* * * * *